United States Patent
Darsow

[11] Patent Number: 5,606,099
[45] Date of Patent: Feb. 25, 1997

[54] PROCESS FOR THE PREPARATION OF SUCCINIC ACID DIALKYL ESTERS

[75] Inventor: Gerhard Darsow, Krefeld, Germany

[73] Assignee: Bayer Aktiengesellschaft, Leverkusen, Germany

[21] Appl. No.: 603,942

[22] Filed: Feb. 20, 1996

[30] Foreign Application Priority Data

Feb. 22, 1995 [DE] Germany .................. 195 06 096.2

[51] Int. Cl.$^6$ .................................................. C07C 69/34
[52] U.S. Cl. .................................... 560/190; 554/121
[58] Field of Search ............................ 560/190; 554/121

[56] References Cited

U.S. PATENT DOCUMENTS 3,830,830  8/1974  Cleveland et al. .

FOREIGN PATENT DOCUMENTS 0008727  3/1980  European Pat. Off. .
0190424  8/1986  European Pat. Off. .

OTHER PUBLICATIONS

Chemical Abstracts, vol. 92, abstract No. 92:214359x, abstract of DE 2,837,022 (corresponds to EP '727), (1980).
Chemical Abstracts, vol. 105, abstract No. 105:152552F, abstract of DE 3,503,485 (corresponds to EP 190 424), (1986).

*Primary Examiner*—Samuel Barts
*Attorney, Agent, or Firm*—Sprung Horn Kramer & Woods

[57] ABSTRACT

Maleic acid dialkyl esters can be hydrogenated by a catalysed liquid phase hydrogenation with hydrogen to give succinic acid dialkyl esters by carrying out the hydrogenation continuously under a pressure of 50 to 400 bar at a reaction temperature of 30° to 160° C. over oxygen-free and support-free shaped bodies, arranged in a fixed bed, of compressed powders of elements of the iron sub-group of sub-group VIII of the Periodic Table or their alloys or mixtures with one another or their alloys or mixtures with elements of sub-group VI, and in addition hydrogenation-inert elements can be present. The shaped bodies have a compressive strength of 20 to 250 N and an internal surface area of 10 to 80 m$^2$/g.

14 Claims, No Drawings

PROCESS FOR THE PREPARATION OF SUCCINIC ACID DIALKYL ESTERS

BACKGROUND OF THE INVENTION

1. Field of the Invention

The present invention relates to an inexpensive, continuously operating process for the preparation of succinic acid dialkyl esters from maleic acid dialkyl esters in which only very small amounts of the butane-1,4-diol usually formed during hydrogenation of maleic acid esters and no mono- and no hydroxycarboxylic acids of C numbers <4 are formed.

Succinic acid dialkyl esters are important, readily biologically degradable solvents for paints and plasticizers for thermoplastic polyesters having particular mechanical and chemical properties.

2. Description of the Related Art

It is known to prepare succinic acid dialkyl esters by esterification of succinic acid or succinic anhydride with the corresponding monoalcohols, acid components often being employed as esterification catalysts and high excesses of alcohol being used. It is furthermore known to hydrogenate maleic acid dialkyl esters discontinuously with hydrogen in a suspension process with a pulverulent $Pd/A_2O_3$ catalyst to give the corresponding succinic acid dialkyl esters (EP 190 424).

The course of the reaction can be illustrated by the following equation:

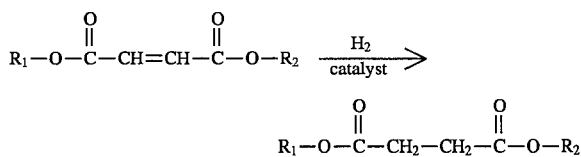

In this equation, $R_1$ and $R_2$ can be identical or different n- or iso-alkyl radicals of C numbers 1 to 12 or cyclic alkyl radicals of C numbers 3 to 6.

Discontinuous processes have the disadvantage that their capacity is very low in relation to the reaction volume and there is therefore a need for large reaction apparatuses and storage tanks. The energy consumption and personnel requirement are relatively high.

Continuous pulverulent catalyst processes which operate with several hydrogenation reactors connected in cascade avoid some of these disadvantages. However, there is still the need for the pulverulent catalysts to be metered in several times in a controlled manner, pumped in circulation and filtered off quantitatively from the reaction product. The catalyst sludge pumps are subject to high mechanical wear. Quantitative removal of the pulverulent catalysts from the reaction product is expensive. Furthermore, the risk of the catalyst activity being reduced relatively rapidly by the additional operations is high. It is therefore advantageous to allow the reaction to proceed over catalysts arranged in a fixed bed. Such catalysts must have a high activity, which should not decrease over a relatively long period of time, because frequent changes of catalyst are likewise expensive in fixed bed reactions.

SUMMARY OF THE INVENTION

Surprisingly, it has now been found that maleic acid dialkyl esters can be hydrogenated continuously in high yields over support-free shaped bodies, arranged in a fixed bed, of oxygen-free metal powders of one or more elements of the iron subgroup of sub-group VIII of the Periodic Table (Mendeleev) to give the corresponding succinic acid dialkyl esters. It may be beneficial here to alloy the metals of the iron sub-group with activating elements of sub-group VI of the Periodic Table. The powders employed here can additionally comprise small contents of elements having no catalytic action (for example silicon, aluminium, titanium or carbon) without the high activity being reduced. The solids must have a compressive strength of 20–250N and an internal surface area of 10–80 $m^2/g$.

Maleic acid dialkyl esters having a purity of ≧99% are preferably employed. However, maleic acid dialkyl esters of lower purity can also be reacted virtually quantitatively.

The invention thus relates to a process for the continuous preparation of succinic acid dialkyl esters by catalytic hydrogenation of maleic acid dialkyl esters, which is characterized in that the hydrogenation is carried out in the liquid phase under an $H_2$ pressure of 50 to 400 bar, with 20 to 60 times the molar amount of $H_2$, based on the stoichiometric amount, and at a temperature of 30 to 160° C. over oxygen-free and support-free catalysts which are arranged in a fixed bed, are present in the form of compressed shaped bodies produced from metal powders and having a compressive strength of 20 to 250N and an internal surface area of 10 to 80 $m^2/g$, and in which the metal powders comprise 60 to 100% by weight of one or more iron metals, 0 to 15% by weight of one or more metals of sub-group VI and 0 to 25% by weight of one or more hydrogenation-inert elements from the group consisting of aluminium, silicon, titanium and carbon, all based on the total weight of the metal powder.

DETAILED DESCRIPTION OF THE INVENTION

The compressive strength of the support-free shaped bodies can be determined in accordance with DIN 50 106.

Support-free shaped bodies can be investigated for the internal surface areas as claimed and therefore their usability for the process according to the invention by known methods which have been described by F. M. Nelsen and F. T. Eggertsen, Analyt. Chem. 30 (1958), pages 1387–1390 or S. J. Gregg and K. S. W. Sing, Adsorption, Surface Area and Porosity, London 1982, Chapters 2 and 6.

The iron sub-group of sub-group VIII of the Periodic Table (Mendeleev) contains the elements iron, cobalt and nickel. The support-free shaped bodies to be used according to the invention comprise one or more of these metals in amounts of at least 60, preferably at least 70, in particular at least 80% by weight, based on the total weight of the support-free shaped bodies.

Sub-group VI of the Periodic Table contains the elements chromium, molybdenum and tungsten. The support-free shaped bodies to be used according to the invention comprise one or more of these metals in amounts of 0–15% by weight. If these are present, the metal powders comprise at least 0.1, preferably at least 0.3, in particular at least 0.5% by weight, based on the support-free shaped bodies; they comprise one or more of these metals in amounts of not more than 15, preferably not more than 10 and in particular not more than 5% by weight, based on the support-free shaped bodies.

The support-free shaped bodies to be used according to the invention can furthermore comprise—in each case based on the support-free shaped bodies—up to 25, preferably up to 15% by weight of other elements; examples of such elements, which do not have a catalytic action, include aluminium, silicon, titanium and carbon. According to a preferred embodiment, the support-free shaped bodies comprise not more than 10% by weight of aluminium and not more than 5% by weight of other elements, in addition to the metals of sub-groups VIII and VI.

Pure hydrogen precompressed to a pressure of 50–400 bar, preferably 100 to 300 bar, is employed for the hydrogenation process, 20 to 60 times, preferably 20 to 40 times the molar amount of hydrogen, based on the stoichiometric amount, being employed.

The hydrogenation is carried out continuously in a fixed bed process over the support-free shaped bodies of the nature described, which serve as hydrogenation catalysts, by a procedure in which either the liquid maleic acid dialkyl esters to be hydrogenated are allowed to flow in cocurrent with the previously admixed hydrogen from the bottom rising upwards over the shaped bodies packed in the hydrogenation reactor, or are passed in from the bottom against the hydrogen flowing in from the top (countercurrent process).

The process according to the invention can of course also be carried out in solvents. Suitable solvents which are inert under the reaction conditions are, for example, di-n-propyl ether, di-iso-propyl ether, di-n-butyl ether, tetrahydrofuran, dioxane and γ-butyrolactone. The process can also be carried out in the presence of the succinic acid dialkyl ester to be formed.

The hydrogenation process is carried out at temperatures from 30° to 160° C., preferably 40° to 100° C. Lower temperatures cause higher residence times or the relinquishing of a quantitative conversion. Higher temperatures lead to the formation of butane-1,4-diol and ester alcohol as by-products.

The hourly catalyst loading can be 200 to 500 g of maleic acid dialkyl ester/l of catalyst.

The hydrogenation reactor can either be an individual high pressure tube of steel or a steel alloy completely or partly packed with the support-free shaped bodies, in which case the use on racks (wire baskets or the like) may also be beneficial, or a jacketed high pressure tube bundle, the individual tubes of which are completely or partly packed with shaped bodies.

The support-free shaped bodies can be produced by customary methods by compression of the metal powders on tablet-making and pelleting machines under high pressure, it also being possible for graphite to be employed in amounts of 0.5–1.5% by weight, based on the total weight of the constituents forming the catalyst, or adhesives to be employed in small amounts, in order to improve the adhesion of the metal particles. The support-free shaped bodies are preferably produced in an oxygen-free atmosphere in order to avoid oxidation reactions on the surface. Tabletted and pelleted shaped bodies having diameters of 3 to 7 mm are most effective and are most favourable for the reaction procedure. The compressive strength of the shaped bodies is of considerable importance, and according to the invention should have values of 20 to 250N, preferably 110 to 220N. Lower compressive strengths lead to disintegration of the shaped bodies or erosive abrasion, which would cause metallic contamination of the reaction product. Higher values cause a disproportionate expenditure during compression without further advantages being achieved. The internal surface area of the shaped bodies is furthermore of considerable importance, and according to the invention has values of 10 to 90 $m^2/g$ and is decisive for the highest possible quantitative conversion of the starting substances. Macroscopically, the shaped bodies have a smooth surface.

Under the reaction conditions described, completely unexpectedly high catalyst service lives of 15,000 hours and more are to be achieved in this manner, which leads to catalyst consumptions of <0.1% by weight, based on the reaction product prepared; it has not yet been possible to achieve such low catalyst consumptions to date in the hydrogenation of maleic acid esters.

The reaction mixture leaving the hydrogenation reactor is let down, the excess hydrogen being able to be collected and, after compression and replacement of the hydrogen consumed, used again. At a conversion of 99.9 to 100%, the reaction mixture comprises succinic acid dialkyl esters to the extent of at least 99% by weight.

In contrast to support-containing catalysts, the oxygen-free and support-free fixed bed catalysts to be employed according to the invention do not tend towards "bleeding", i.e. transfer of catalyst constituents in ionic or colloidal form into the solution phase of the substrate, so that the substrate is not contaminated by heavy metals, which can usually likewise be removed from the substrate only with great effort, for example with the aid of ion exchangers. The catalyst metals to be employed can easily be worked up, for example after prolonged use of the catalyst, and re-used, since the heavy metals do not have to be separated from a support material in a cumbersome manner. In the case of polyfunctional compounds, for example only partly esterified polyhydric alcohols, the tendential formation, with heavy metal ions, of complex chelate compounds of the fatty soaps, which can be removed from the esters or ester mixtures only with difficulty, formed was a further fear; this fear does not arise with the catalysts to be employed according to the invention.

The succinic acid dialkyl esters produced are obtained in a purity of ≧99.9% by weight after removal of a small amount of low-boiling first runnings and if appropriate after-runnings by distillation, and can be employed in this quality for all processes for their further processing.

EXAMPLES.

Example 1

A vertical, thermally insulated high pressure tube of rustproof steel of 45 mm internal diameter and 1 m length was packed with 1.4 l of a hydrogenation catalyst which was produced by tabletting Ni powder and had, at a cylinder height of 5 mm and a diameter of 5 mm, a compressive strength of 147N on the cylinder surface and an internal surface area of 33 $m^2/g$. 480 g of dimethyl maleate (purity ≧99.5% by weight) per hour were pumped through this tube from the bottom upwards together with 20 times the molar amount of highly pure hydrogen under a pressure of 300 bar.

Dimethyl maleate and hydrogen were first passed together through a heat exchanger and were heated such that they entered the high pressure tube with a temperature of 40° C. The mixture of liquid reaction product and excess hydrogen leaving the high pressure tube was passed to a separator from where the hydrogen, after replacement of the amount consumed, was pumped back together with fresh dimethyl maleate into the preheater and from there again into the high pressure tube.

After letting down to normal pressure and cooling, the colourless and clear liquid of the reaction product was analysed by gas chromatography. It comprised 0.2% by weight of methanol and 0.1% by weight of butane-1,4-diol as alcoholic secondary constituents. The dimethyl maleate content of the organic reaction product was <0.1% by weight, so that the dimethyl succinate content was >99.6% by weight. After removal of the secondary constituents by distillation, the dimethyl succinate produced was obtained in a purity of 99.9% by weight and had a boiling point of 196° C.

Example 2

In a high pressure tube as in Example 1, the hydrogen was passed in the reverse reaction flow to that in Example 1 against the ascending dimethyl maleate at a temperature of 45° C. under a hydrogen pressure of 200 bar, the same amount as in Example 1 being hydrogenated per hour. The catalyst had been produced by tabletting a pulverulent Ni/Fe alloy. The alloy comprised an iron content in nickel of 15% by weight. At a cylinder height of 5 mm and a diameter of 5 mm, the tablets had a compressive strength of 137N on the cylinder surface and an internal surface area of 74 m$^2$/g.

After a running time of 3400 hours, the conversion of the dimethyl maleate employed was 99.95% by weight. The content of methanol in the reaction product was 0.20% by weight and the butane-1,4-diol content was 0.15% by weight, so that the dimethyl succinate content of the reaction product was 99.60% by weight. After removal of the impurities by distillation, the dimethyl succinate produced was obtained in a purity of 99.9% by weight.

Example 3

A vertical, thermally insulated high pressure tube of rustproof steel of 45 mm internal diameter and 1 m length was packed with 1.4 l of a hydrogenation catalyst which was produced by tabletting powder of an Ni/Mo alloy with an Mo content of 1.75% and had, at a cylinder height of 5 mm and a diameter of 5 mm, a compressive strength of 191N and an internal surface area of 58 m$^2$/g. 590 g of diethyl maleate per hour were pumped through this tube from the bottom upwards together with 30 times the molar amount of highly pure hydrogen under a pressure of 300 bar.

Diethyl maleate and hydrogen were brought to a temperature of 55° C. before entry into the high pressure tube.

After a running time of 1600 hours, the conversion of the diethyl maleate employed was 100% by weight. The content of ethanol in the reaction product was 0.3% by weight and the content of butane-1,4-diol was 0.1% by weight, so that the diethyl succinate content was 99.6% by weight. After removal of the impurities by distillation, the diethyl succinate isolated was obtained in a purity of 99.9% by weight. It had a boiling point of 217° C.

Example 4

In a high pressure tube as in Example 1, the same amount of diethyl maleate per hour was hydrogenated at a temperature of 45° C. under a hydrogen pressure of 200 bar. The catalyst was produced by tabletting a pulverulent Ni/Fe/Mo alloy.

The alloy comprised an Fe content in Ni of 15% and an Mo content of 1.4%. At a cylinder height of 3 mm and a diameter of 3 mm, the tablets had a compressive strength of 162N and an internal surface area of 68 m$^2$/g.

After a running time of 1600 hours, the conversion of the diethyl maleate employed was 99.9% by weight. The content of ethanol in the reaction product was 0.2% by weight and the content of butane-1,4-diol was 0.1% by weight, so that the diethyl succinate content of the reaction product was 99.6% by weight.

Example 5

In a high pressure tube as in Example 1, but of high pressure steel N 9, the same amount of di-n-butyl maleate per hour was hydrogenated at a temperature of 50° C. under a hydrogen pressure of 300 bar. The catalyst was produced by tabletting powder of an Ni/Mo/Al alloy with an Mo content of 1.02% by weight and an Al content of 5.1% by weight. At a cylinder height of 5 mm and a diameter of 5 mm, the tablets had a compressive strength of 210N and an internal surface area of 71 m$^2$/g.

After a running time of 2400 hours, the content of di-n-butyl succinate in the reaction product was 99.6% by weight. After removal of the impurities by distillation, the di-n-butyl succinate produced was obtained in a purity of 99.9% by weight (boiling point$_4$: 108° C.).

Example 6

In a high pressure tube as in Example 1, an amount of 360 g of dimethyl maleate per hour was hydrogenated at a temperature of 45° C. under a hydrogen pressure of 300 bar. The catalyst was produced by tabletting a pulverulent Ni/Al alloy with an Al content of 6.1% by weight. At a cylinder height of 3 mm and a diameter of 3 mm, the tablets had a compressive strength of 156N on the cylinder surface and an internal surface area of 69 m$^2$/g.

After a running time of 1140 hours, the conversion of the dimethyl maleate employed was 99.9% by weight. After distillation of the crude dimethyl succinate, this had a purity of 99.9% by weight and a boiling point of 196° C.

Example 7

In a high pressure tube as in Example 1, an amount of 420 g of di-n-propyl maleate per hour was hydrogenated at a temperature of 55° C. under a hydrogen pressure of 200 bar. The catalyst was obtained by tabletting a powdered Ni/Al Si alloy with an Al content of 5.4% by weight and an Si content of 0.2% by weight. At a cylinder height of 3 mm and a diameter of 3 mm, the tablets had a compressive strength of 148N and an internal surface area of 61 m$^2$/g.

After a running time of 1900 hours, the conversion of the di-n-propyl maleate employed was >99.0% by weight. The content of n-propanol in the reaction product was 0.3% by weight and the content of butane-1,4-diol was 0.18% by weight, so that the di-n-propyl succinate content was $\geq$99.42% by weight. After distillation of the crude di-n-propyl succinate, this had a boiling point of 248° C.

What is claimed is:

1. A process for the continuous preparation of a succinic acid dialkyl ester by catalytic hydrogenation of a maleic acid dialkyl ester, wherein the hydrogenation is carried out in the liquid phase under a H$_2$ pressure of 50 to 400 bar, with 20 to 60 times the molar amount of H$_2$, based on the stoichiometric amount, and at a temperature of 30° to 160° C. over an oxygen-free and support-free catalyst which is arranged in a fixed bed, is present in the form of compressed shaped bodies produced from metal powder and having a compressive strength of 20 to 250N and an internal surface area of 10 to 80 m$^2$/g, and in which the metal powder comprises 60 to 100% by weight of one or more iron metals, 0 to 15% by weight of one or more metals of sub-group VI and 0 to 25% by weight of one or more hydrogenation-inert elements from group consisting of aluminium, silicon, titanium and carbon, all based on the total weight of the metal powder.

2. The process of claim 1, wherein the metal powder comprises 70 to 100% by weight of one or more iron metals.

3. The process of claim 2, wherein the metal powder comprises 80 to 100% by weight of one or more iron metals.

4. The process of claim 1, wherein, if metals of sub-group VI are present, the metal powder comprises a content of 0.1 to 15% by weight thereof.

5. The process of claim 4, wherein the metal powder comprises a content of 0.3 to 10% by weight of sub-group VI metals.

6. The process of claim 5, wherein the metal powder comprises a content of 0.5 to 5% by weight of sub-group VI metals.

7. The process of claim 1, wherein if hydrogenation-inert elements are present, the metal powder comprises a content of 0 to 10% by weight of aluminium and of 0 to 5% by weight of each of the elements Si, Ti and C.

8. The process of claim 7, wherein the total content of the hydrogenation-inert elements is 0 to 15% by weight.

9. The process of claim 8, wherein the total content of the hydrogenation-inert elements is 0 to 10% by weight.

10. The process of claim 1, wherein the shaped bodies are those having a compressive strength of 110 to 220N.

11. The process of claim 1, wherein the shaped bodies are cylindrical or spherical and have diameters of 3 to 7 mm.

12. The process of claim 1, wherein the hydrogenation is carried out under an $H_2$ pressure of 100 to 300 bar.

13. The process of claim 1, which is carried out with 20 to 40 times the molar amount of $H_2$.

14. The process of claim 1, wherein the unsaturated fatty acid ester to be hydrogenated is passed through the hydrogenation reactor from the bottom upwards, while the hydrogenation required for the hydrogenation is either pumped into the reactor together with the unsaturated ester of passed against this from the top flowing downwards.

* * * * *